United States Patent [19]

Anderson

[11] Patent Number: 5,171,922

[45] Date of Patent: Dec. 15, 1992

[54] PROCESS FOR SEPARATING PARA-XYLENE FROM A $C_8$ AND $C_9$ AROMATIC MIXTURE

[75] Inventor: Gary C. Anderson, Clarendon Hills, Ill.

[73] Assignee: UOP, Des Plaines, Ill.

[21] Appl. No.: 791,697

[22] Filed: Nov. 14, 1991

[51] Int. Cl.[5] .................. C07C 7/04; C07C 7/13
[52] U.S. Cl. ........................... 585/805; 585/820; 585/826; 585/828
[58] Field of Search ............... 585/820, 805, 826, 828

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,422,848 | 1/1969 | Liebman et al. | 137/625.15 |
| 3,686,342 | 8/1972 | Neuzil | 260/674 SA |
| 3,706,812 | 12/1972 | De Rosset et al. | 260/674 SA |
| 4,159,284 | 6/1979 | Seko et al. | 585/478 |
| 4,381,419 | 4/1983 | Wylie | 585/826 |
| 4,402,832 | 9/1983 | Gerhold | 210/659 |
| 4,478,721 | 10/1984 | Gerhold | 210/659 |
| 4,642,397 | 2/1987 | Zinnen et al. | 568/934 |
| 4,864,069 | 9/1989 | Zinnen | 585/828 |
| 4,886,930 | 12/1989 | Zinnen | 585/828 |
| 5,012,038 | 4/1991 | Zinnen | 585/828 |
| 5,057,643 | 10/1991 | Zinnen | 585/828 |
| 5,107,062 | 4/1992 | Zinnen | 585/828 |

Primary Examiner—Anthony McFarlane
Attorney, Agent, or Firm—Thomas K. McBride; John F. Spears, Jr.; Jack H. Hall

[57] ABSTRACT

In the process flow scheme for chromatographically separating paraxylene from $C_8$ isomers containing substantial amounts of $C_9$ aromatic hydrocarbon impurities with an X or Y zeolite adsorbent and heavy desorbents, e.g., tetralin and derivatives thereof and diethyltoluene, a drag stream is split from the extract fractionation column bottoms stream, containing desorbent and $C_9$ aromatic hydrocarbon impurities for recycling to the separation unit, and is directed to the raffinate fractionation column, where $C_9$ aromatic hydrocarbons are removed to prevent $C_9$ aromatic hydrocarbons from building up in the desorbent input to the separation unit. A fractionator for the extract column stream is eliminated, lowering capital costs.

6 Claims, 1 Drawing Sheet

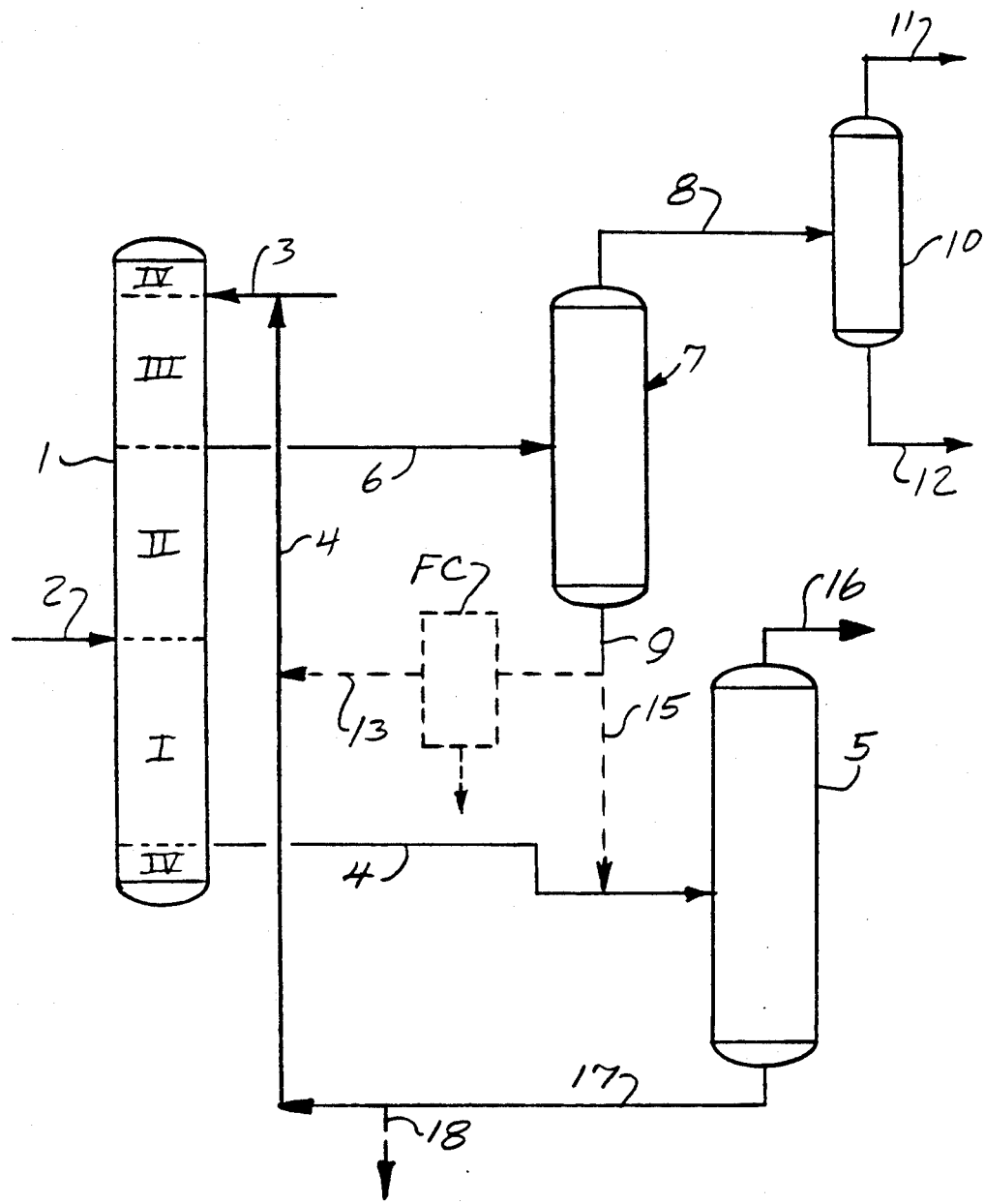

PROCESS FOR SEPARATING PARA-XYLENE FROM A $C_8$ AND $C_9$ AROMATIC MIXTURE

FIELD OF THE INVENTION

The present invention pertains to a process for the separation and recovery of para-xylene from a mixture of xylene isomers, including ethylbenzene, and especially those containing additional amounts of impurities in the form of $C_9$ aromatic hydrocarbons. In particular, the process pertains to an adsorptive separation utilizing molecular sieve adsorbents and heavy desorbents to obtain para-xylene in relatively pure state from a mixture of xylene isomers and aromatic hydrocarbon impurities.

BACKGROUND OF THE INVENTION

In numerous processes described in the patent literature, X and Y zeolitic adsorbents exchanged with various cations are used with certain desorbents to separate the para-isomer of dialkyl-substituted monocyclic aromatics from the other isomers, particularly para-xylene from other xylene isomers. For example, in Neuzil et al U.S. Pat. No. 3,686,342, para-diethylbenzene is the preferred desorbent. More recently, in Zinnen U.S. Pat. Nos. 4,886,930; 4,864,069; 5,012,038 and U.S. Pat. No. 5,057,643, other "heavy" desorbents, e.g., diethyltoluene and tetralin and tetralin derivatives, have been disclosed for a process for separating para-xylene where the feed mixtures contain higher boiling aromatic hydrocarbons such as $C_9$ aromatics, $C_{10}$ aromatics, etc. With these $C_9$ and higher aromatic impurities in the feed, it is difficult to separate the desorbent, p-DEB, from the $C_9^+$ aromatics by fractionation because the boiling points of these materials are so close. If not removed, the $C_9$ aromatics would gradually build up in the desorbent, which must be recycled to the separation process for economic reasons.

U.S. Pat. No. 4,864,069 to Zinnen discloses a process for separating para-xylene from a mixture of xylene isomers with diethyltoluene as a heavy desorbent in which the heavy desorbent is recovered and recycled to the process by fractionating the raffinate to separate the desorbent from the xylene isomers and $C_9$ impurities. Likewise, after the para-xylene is removed from the extract in the extract column, the bottoms of the extract column (fractionation) contain desorbent and $C_9$ aromatic impurities which is further fractionated to recover the desorbent for return to the adsorbent separation process. In the present invention, the step of fractionating the extract bottoms to remove $C_9$ aromatic impurities from the desorbent recycle stream is eliminated with only a small added duty imposed on the raffinate column.

In U.S. Pat. Nos. 4,886,930 and 5,057,643 to Zinnen, heavy desorbents, tetralin and alkyl derivatives of tetralin, were disclosed for use in the separation of para-xylene from mixtures of xylene isomers. The recovery of the heavy desorbent from raffinate and extract streams by simple fractionation is also contemplated there.

It is also known that crystalline aluminosilicates, i.e., or zeolites, are used in adsorption separations of various mixtures in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type, water permeable organic polymers or silica are generally used.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The invention may also be practiced in a cocurrent, pulsed batch process, like that described in U.S. Pat. No. 4,159,284 or in a cocurrent, pulsed continuous process, like that disclosed in Gerhold U.S. Pat. Nos. 4,402,832 and 4,478,721.

The functions and properties of adsorbent and desorbents in the chromatographic separation of liquid components are well-known, but for reference thereto, Zinnen et al U.S. Pat. No. 4,642,397 is incorporated herein.

I have discovered a process for separating para-xylene from its isomers including ethylbenzene and $C_9$ aromatics employing a zeolite adsorbent and a heavy desorbent whereby substantial economies can be obtained by the elimination of a desorbent fractionating column.

SUMMARY OF THE INVENTION

In brief summary, the invention is a chromatographic process for separating p-xylene from a feed mixture comprising p-xylene and one or more additional xylene isomers (including ethylbenzene) and $C_9$ aromatic hydrocarbons comprising contacting the feed mixture with a zeolite adsorbent capable of effecting the selective adsorption of the p-xylene, removing a raffinate stream comprising the less selectively-adsorbed $C_8$ and $C_9$ isomers and desorbent from contact with the adsorbent, contacting the adsorbent with a desorbent having a higher boiling point than the $C_9$ aromatic hydrocarbons, preferably comprising diethyltoluene, tetralin or alkyl derivatives of tetralin, mixtures thereof or mixtures thereof with a normal paraffin, at desorption conditions, to effect the removal of an extract stream, comprising para-xylene, $C_9$ aromatic hydrocarbons and desorbent, fractionating the extract stream in an extract fractionator to produce an extract overhead stream comprising para-xylene and an extract bottoms stream comprising $C_9$ aromatic hydrocarbons and desorbent, combining at least about 25 (wt.) % to about 80 (wt.) % of the extract bottoms stream with the raffinate stream and directing the combined streams to the raffinate fractionator and fractionating the combined stream in a raffinate fractionator to produce an overhead stream comprising the less selectively adsorbed $C_8$ isomers and $C_9$ aromatic hydrocarbons and a raffinate bottoms stream comprising desorbent. The remainder of the extract bottoms stream is recycled to the separation zone. By directing a portion of the extract bottoms stream to the raffinate fractionator, it is possible to eliminate a fractionator, normally employed to separate the $C_9$ aromatics from the desorbent and eliminate at least part of the $C_9$ aromatics from the system prior to recycling the desorbent to the separation column to avoid a buildup of the $C_9$ aromatics in the desorbent.

BRIEF DESCRIPTION OF THE DRAWING

The FIGURE is a flow scheme representing the process for separating para-xylene chromatographically from its isomers and $C_9$ aromatic hydrocarbons in which the bottoms from the extract fractionation column, containing desorbent and $C_9$ aromatic hydrocarbons, is split and a drag stream from the desorbent recycle stream is directed to the raffinate fractionation column.

DETAILED DESCRIPTION OF THE INVENTION

A well-known separation process for recovering para-xylene from a mixture of xylene isomers utilizing zeolitic selective adsorbents and a higher boiling desorbent, a countercurrent continuous simulated moving bed process, such as disclosed in Broughton U.S. Pat. No. 2,985,589, is preferred in the practice of the invention.

In the figure, showing the flow scheme of the present invention, the separation unit 1 can be a column containing a number of separate beds of an adsorbent, selective for p-xylene, each having inlet and outlet means. The inlet and outlet means are connected by conduits to valve means, such as a rotary valve described in Carson et al U.S. Pat. No. 3,040,777 or Liebman et al U.S. Pat. No. 3,422,848, regulated by control means to direct feed and desorbent streams to the appropriate beds and withdrawing extract and raffinate output streams from the appropriate beds. Bed movement is simulated by periodically advancing the actual points of liquid addition and withdrawal to respective points in the next bed in a direction so that the apparent movement of adsorbent is opposite the direction of the fluid flow in the column. That is, each inlet and outlet means is shifted by one bed in the same direction as fluid flow. Fluid flow in column 1 is downwardly. Operational zones in the adsorbent column are defined by the position of the input and output streams as follows: adsorption zone I is the adsorbent between the feed inlet and raffinate outlet; purification zone II is the adsorbent between the feed inlet and the extract outlet and is located immediately upstream of zone I; desorption zone III is the adsorbent between the extract outlet and the desorbent inlet and is located directly upstream of zone II. A buffer zone IV is optional, but where used is the adsorbent between the desorbent inlet and the raffinate outlet. Although not shown in the drawing, the top and bottom of the column are interconnected for continuous liquid flow in the column and pump means may be installed in the interconnection to ensure continuous flow in the desired direction.

Adsorbents which may be used in the process are crystalline aluminosilicates, e.g., X and Y zeolites containing Group IA or IIA metal ions at exchangeable cation sites. The preferred exchange ions are barium, potassium or a mixture thereof. Others which are selective for the p-xylene isomer are also suitable for use in the invention.

Feed is directed into the column 1 through input line 2. The feed may be prefractionated to remove high boiling components, such as $C_{10}$ or higher aromatics in a simple, low cost column, not shown. Although feeds containing as much as 25% $C_9$ aromatics may be handled by this process, it is more economical to reduce $C_9$ aromatics in the feed to separation column 1 in a prefractionation column (not shown) to 5% or less, preferably about 2–5% (wt.). Feeds containing less than about 0.1% (wt.) $C_9$ aromatic hydrocarbons do not present a problem of buildup and therefore feeds having at least about 0.1% (wt.) $C_9$ aromatics are contemplated for use in this process. The greatest need, in terms of economic benefit, for this process is in the purification of feedstreams containing substantial amounts of $C_9$ aromatic hydrocarbons, e.g., 2% (wt.) or greater. Suitable feed materials for the process include crystallizer mother liquors, reformates and isomerates containing a mixture of $C_8$ isomers from which it is desired to separate highly pure p-xylene.

Desorbent is directed into the column 1 through input line 3. The desorbents are heavy desorbents, i.e., have a boiling point greater than the $C_9$ aromatics, making it possible to separate the $C_9$ aromatics from the desorbent by simple fractionation and avoid building up $C_9$ aromatic hydrocarbons in the recycled desorbent stream. In the preferred isothermal, isobaric, liquid-phase operation of the process of this invention, when the feed material to the separation process contains substantial amounts of $C_9$ aromatics, the preferred desorbent materials are diethyltoluene isomers and mixtures thereof, tetralin and alkyl or dialkyl derivatives of tetralin and mixtures thereof. The desorbent may also be diluted with a normal paraffin, e.g., n-heptane, to modify the desorbent strength.

The preferred diethyltoluenes contain at least about 40% (wt.) of one or more of the following isomers: 2,3-diethyltoluene (DET), 2,5-DET and 2,6-DET.

Suitable alkyl-substituted derivatives of tetralin include methyl tetralin, ethyl tetralin, propyl tetralin, isopropyltetralin, etc. Suitable dialkyl-substituted derivatives of tetralin include methyl ethyl tetralin, dimethyl tetralin, diethyltetralin, etc. Mixtures of tetralin with one or more of these derivatives, as well as mixtures of these derivatives also may be used with good results.

All position isomers and mixtures are intended to be included when diethyltoluene or any tetralin derivative is referred to herein.

Adsorption conditions will include a temperature range of from about 20° to about 250° C. with about 60° to about 200° C. being more preferred and a pressure just sufficient to maintain liquid phase, which may be from about atmospheric to 600 psig. Desorption conditions will include the same range of temperatures and pressure as used for adsorption conditions.

A raffinate stream 4, comprising the least strongly adsorbed components, ethylbenzene and o- and m-xylene, most of the $C_9$ aromatics, except p-ethyltoluene, and desorbent, is withdrawn from the column 1 at the downstream end of zone I and is directed to a raffinate fractionation column 5.

An extract stream 6, comprising the most strongly adsorbed feed components, p-xylene and p-ethyltoluene, and desorbent, is withdrawn from column 1 at the downstream end of zone III and is directed to an extract fractionation column 7. In the fractionation column 7, the extract stream is split into an extract overhead stream 8, comprising p-xylene and any lighter fractions from the feed that were as strongly adsorbed as the p-xylene, for example, toluene and an extract bottoms stream 9 comprising mainly desorbent and the strongly adsorbed $C_9$ aromatics, e.g., p-ethyltoluene. In many cases, the feed is prefractionated to remove light fractions, such as toluene and benzene, and therefore the extract overhead stream 8 will contain substantially only p-xylene product at 99% purity or higher. If lighter components remain, however, they may be separated from the p-xylene product by a simple fractionation in column 10 into a light fraction stream 11 and extract product stream 12.

The extract bottoms stream 9 from extract fractionator 7 contains desorbent and $C_9$ aromatics. Prior to our invention, the $C_8$ aromatics would be removed from the desorbent, before the desorbent is returned to the adsorbent column 1 in order to avoid the buildup of $C_9$ aromatics in the adsorbent column. Since additional $C_9$ aromatics are brought into the system in the feed, if the $C_9$ aromatics are not removed from the system, they will gradually build up in the adsorbent column, effectively removing a greater and greater portion of the adsorbent capacity. Thus, previously, $C_9$ aromatics would be removed from the extract column bottoms stream by fractionation, e.g., in a feed prefractionation unit or in a column FC, shown in dashed lines. According to the invention, however, the column FC may be eliminated, thereby reducing costs, without subjecting the process to the foregoing problem of $C_9$ aromatic buildup, by directing at least a portion of the extract bottoms stream to the raffinate column 5 where $C_9$ aromatics are removed overhead with the raffinate components. The raffinate components and the $C_9$ aromatics may then be isomerized to obtain additional feed to the separation step. However, the increase in the raffinate column size and energy requirements is considerably less overall than the prior $C_9$ aromatics separation scheme.

The extract bottoms stream 9 is divided into two streams, the first, a desorbent recycle stream 13 which is directed back into the separation column 1 via lines 14 and 3 and the second, a so-called drag stream 15 which is combined with the raffinate stream 4 and directed to the raffinate fractionation column 5. The respective amounts of the extract bottoms stream 9 directed to line 13 to be recycled with desorbent and to line 15 to be directed to the raffinate fractionation column can be varied by appropriate control means, for example, valve means actuated by an analyzer.

In fractionation column 5, raffinate materials, o- and m-xylene and ethylbenzene, and most of the $C_9$ aromatics, including p-ethyltoluene from drag stream 15, are recovered in the raffinate column overhead 16 and may be directed to an isomerization process along with the light overhead 11 from column 10 to be converted to additional p-xylene-rich feed for the separation process. Desorbent is removed from fractionation column 5 in the raffinate column bottoms stream 17 and directed back into the separation column 1 via lines 14 and 3. A small portion of the desorbent recycle stream 17 may be removed from the system via line 18 and periodically treated, e.g., by fractionation, to remove any impurities, such as $C_{12}$ aromatics which have built up in the desorbent.

In the practice of the invention, from about 25% to about 80% of the extract column bottoms stream 9 is diverted to the raffinate column 5 and from about 20% to about 75% is mixed with recycled desorbent from the raffinate column and returned to the adsorbent column. Thus, in the extract column 7, the $C_8$'s and lighter components are split from the heavy desorbent and $C_9$'s and heavier components. In the split obtained in raffinate column 5, the heavy desorbent is taken from the bottom while raffinate components and $C_9$ aromatics are removed overhead. The amount of extract column bottoms directed to the adsorbent column is adjusted to maintain a target desorbent purity. The greater the desorbent impurity level permitted, the more bottoms can be mixed with recycled desorbent to be used in the adsorbent column and therefore the lower the fractionation requirement in raffinate column 5. In one study, using 5,000 ppm contaminant level, 28% of the extract bottoms stream is diverted to the raffinate column while 72% is recycled to the desorbent line 14. If the contamination level is reduced to 2,500 ppm, 54% of the extract bottoms stream is diverted to the raffinate column and 46% recycled to the desorbent line 4. In other cases, under other conditions, from about 25% to about 80% may be diverted to the raffinate column 5. The level of contaminants (mostly $C_9$ aromatics) in the combined (fresh plus recycled) desorbent stream may be adjusted so that the level of $C_9$ aromatics in the feed does not exceed the amount desired for economic operation, e.g., between 2 and 5%, as previously mentioned.

EXAMPLE

This example is a computer simulation to illustrate the preferred embodiment of the process shown in the FIGURE utilizing a continuous simulated moving bed countercurrent type of operation in which a portion of the extract column bottoms is directed to the raffinate fractionation column and the remainder is recycled to the adsorption separation unit 1. The computer simulation makes engineering calculations based on actual experience in operating these components in similar commercial processing units under the selected conditions for the present process. The processing units for the simulation are arranged as in the figure and will be referred to using the reference numbers appearing in the drawing. A reformate having the composition of Table 1 is fed to the separation unit 1 via line 2. Desorbent, tetralin, diluted to 30% with n-heptane, is fed into the column in desorbent stream 3. The separation unit 1 comprises 24 beds filled with BaX zeolite (ADS-27 available from UOP, Des Plaines, IL). The raffinate is withdrawn from the separation unit 1 through line 4 and directed to the raffinate column 5 for fractionation into overhead stream 16, containing $C_{8-10}$ normal paraffins, o- and m-xylene, ethylbenzene, $C_9$ aromatics and bottoms stream 17 comprising desorbent for recycling to the separation unit 1. The extract, which contains p-xylene, desorbent, toluene and $C_9$ aromatic hydrocarbons which are more strongly adsorbed than the extract product, p-xylene, is withdrawn from the separation unit 1 through line 6 and directed to the extract column 7 for fractionation into an extract overhead stream 8 and an extract bottoms stream 9. The extract bottoms stream 9 comprises desorbent and p-ethyltoluene. The extract bottoms stream 9 is split, with 50% (wt.) returned to the desorbent pool through line 13 and combined with desorbent recovered from the raffinate column 5 and fresh desorbent via lines 14 and 3. The remaining 50% (wt.) of the extract bottoms stream 7 is combined with the raffinate stream and directed to the raffinate column 5.

The extract column overhead stream 8 containing p-xylene and toluene is sent to fractionation column 10 where the toluene and any lights are removed and p- xylene product is recovered from line 12 at 99.8% purity. Para-xylene recovery is 97.0%.

The operating conditions for the separation unit are:

| | |
|---|---|
| Temperature: | 350° F. (177° C.) |
| Pressure, psig: | 125 |
| Cycle Time: | 32 min. |

The material balance for the process, based on feed rate of 362,579 lb per hr. and desorbent rate of 453,936 lb per hr. and adsorbent volume of 16804 cu. ft. is set forth in Table 2.

TABLE 1

| Component | Feed Composition | |
|---|---|---|
| | lbs/hr | wt. % |
| $n$-$C_8$ | 3,833 | 1.06 |
| $n$-$C_9$ | 302 | 0.08 |
| $n$-$C_{10}$ | 83 | 0.02 |
| Ethylcyclohexane | 15,330 | 4.23 |
| Toluene | 3,836 | 1.06 |
| p-Xylene (p-X) | 68,872 | 19.00 |
| o-Xylene (o-X) | 65,448 | 18.05 |
| m-Xylene (m-X) | 163,186 | 45.01 |
| Ethylbenzene | 34,425 | 9.49 |
| $C_9$ Aromatics ($C_9$ A) | | |
| n-propyl benzene | 381 | 0.11 |
| isopropyl benzene | 500 | 0.14 |
| o-ethyltoluene | 396 | 0.11 |
| m-ethyltoluene | 1,741 | 0.48 |
| p-ethyltoluene (p-ET) | 866 | 0.24 |
| 1,2,3-Trimethylbenzene | 55 | 0.02 |
| 1,2,4-Trimethylbenzene | 2,018 | 0.56 |
| 1,3,5-Trimethylbenzene | 1,307 | 0.36 |
| TOTAL | 362,579 | 100.00 |

TABLE 2

| Stream and Component | Flow Rate | |
|---|---|---|
| | lbs/hr | wt. % |
| Extract | | |
| Toluene | 2,302 | 1.01 |
| Xylene Isomers: p-X | 66,806 | 29.27 |
| Other (o-X, m-X, Ethylbenzene) | 134 | 0.06 |
| $C_9$ A: p-ET | 1,496 | 0.66 |
| Tetralin | 157,487 | 69.01 |
| Total | 228,225 | 100.00 |
| Extract Column Overhead | | |
| Toluene | 2,302 | 3.32 |
| Xylene Isomers: p-X | 66,806 | 96.48 |
| Other | 134 | 0.19 |
| Total | 69,242 | 100.00 |
| Extract Bottoms Recycle Desorbent | | |
| $C_9$ A: p-ET | 748 | 0.94 |
| Tetralin | 78,743 | 99.06 |
| Total | 79,491 | 100.00 |
| Extract Bottoms to Raffinate Column | | |
| $C_9$ A: p-ET | 748 | 0.94 |
| Tetralin | 78,744 | 99.06 |
| Total | 79,492 | 100.00 |
| Raffinate | | |
| n-paraffins ($n$-$C_{8-10}$) and cyclohexane | 19,548 | 3.32 |
| Toluene | 1,534 | 0.26 |
| Xylene Isomers: p-X | 2,066 | 0.35 |
| Other | 262,925 | 44.64 |
| $C_9$ A: p-ET | 118 | 0.02 |
| Other | 6,398 | 1.09 |
| Tetralin | 296,449 | 50.33 |
| Total | 589,038 | 100.00 |

TABLE 2-continued

| Stream and Component | Flow Rate | |
|---|---|---|
| | lbs/hr | wt. % |
| Raffinate Column Overhead: | | |
| n-paraffins ($n$O$C_{8-10}$) | 19,548 | 6.66 |
| Toluene | 1,534 | 0.52 |
| Xylene Isomers: p-X | 2,066 | 0.70 |
| Other | 262,925 | 89.63 |
| $C_9$ A: p-ET | 866 | 0.30 |
| Other | 6,398 | 2.18 |
| Total | 296,337 | 100.00 |
| Raffinate Bottoms to Recycle Desorbent: | | |
| Tetralin | 375,193 | 100.00 |
| Total | 375,193 | 100.00 |
| Total to Recycle Desorbent: | | |
| $C_9$ A: p-ET | 748 | 0.16 |
| Tetralin | 453,936 | 99.84 |
| Total | 454,684 | 100.00 |

What is claimed:

1. A process for the production and recovery of para-xylene from an aromatic feed stream comprising $C_8$ aromatic hydrocarbons and up to about 25% $C_9$ aromatic hydrocarbons comprising the steps of:
   (a) contacting said feed stream with an adsorbent selective for para-xylene in a separation zone;
   (b) removing a raffinate stream comprising the less selectively adsorbed $C_8$ and $C_9$ isomers and desorbent from contact with said adsorbent;
   (c) contacting said adsorbent with a desorbent having a boiling point higher than said $C_9$ aromatic hydrocarbons, at desorption conditions, to effect the removal of an extract stream comprising para-xylene, $C_9$ hydrocarbons and desorbent;
   (d) fractionating said extract stream in an extract fractionator to produce an extract overhead stream comprising para-xylene and an extract bottoms stream comprising said $C_9$ aromatic hydrocarbons and desorbent;
   (e) combining at least about 25 (wt.) % to about 80 (wt.) % of said extract bottoms stream with said raffinate stream and directing said combined streams to a raffinate fractionator;
   (f) fractionating said combined stream in said raffinate fractionator to produce a raffinate overhead stream comprising said less selectively adsorbed $C_8$ isomers and $C_9$ aromatic hydrocarbons and a raffinate bottoms stream comprising desorbent; and
   (g) recycling the remainder of said extract bottoms stream and said raffinate bottoms stream to step (c) as said desorbent.

2. The process of claim 1 wherein said adsorbent is an X or Y zeolite with Group IA or IIA cations at the cationic exchange sites.

3. The process of claim 1 wherein said desorbent comprises diethyltoluene, tetralin or tetralin derivatives or mixtures thereof and mixtures of said desorbent with a normal paraffin.

4. The process of claim 1 wherein feed components lighter than said $C_8$ aromatics and heavier than $C_9$ aromatics are separated from said feed stream by fractional distillation.

5. The process of claim 1 wherein said feed stream contains from about 2 to about 5% (wt.) $C_9$ aromatic hydrocarbons.

6. The process of claim 1 wherein said feed stream contains at least about 0.1% (wt.) $C_9$ aromatic hydrocarbons.

* * * * *